United States Patent [19]

Shibata et al.

[11] Patent Number: 4,786,730

[45] Date of Patent: Nov. 22, 1988

[54] PYRIMIDINE COMPOUND

[75] Inventors: Toshihiro Shibata; Masaki Kimura, both of Saitama; Norio Kurosawa, Tokyo, all of Japan

[73] Assignee: Adeka Argus Chemical Co., Ltd., Tokyo, Japan

[21] Appl. No.: 136,648

[22] Filed: Dec. 22, 1987

[30] Foreign Application Priority Data

Dec. 26, 1986 [JP] Japan .................. 61-314700

[51] Int. Cl.$^4$ ............... C09K 19/34; G02F 1/13; C07D 239/02
[52] U.S. Cl. ............... 544/335; 252/299.01; 252/299 S; 252/299.61; 350/350 R; 350/350 S; 544/242
[58] Field of Search ........... 252/299.61, 299.5, 299.01; 350/350 R, 350 S; 544/335, 242

[56] References Cited

U.S. PATENT DOCUMENTS 4,725,688 2/1988 Taguchi et al. ................ 252/299.61

FOREIGN PATENT DOCUMENTS 3515373 11/1986 Fed. Rep. of Germany ........................ 252/299.61
61-271279 12/1986 Japan ............................ 252/299.61

Primary Examiner—Teddy S. Gron
Attorney, Agent, or Firm—Young & Thompson

[57] ABSTRACT

The present invention discloses an optically active pyrimidine compound represented by the following general formula:

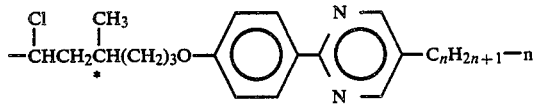

wherein
m is 1 to 12;
n is 4 to 18; and
*C represents an asymmetric carbon atom.

The pyrimidine compound of the present invention is a liquid crystal compound useful as an electrooptic element wherein the response of the ferroelectric liquid crystal to an electric field is utilized.

4 Claims, No Drawings

PYRIMIDINE COMPOUND

BACKGROUND OF THE INVENTION

1. Field of the Invention

This invention relates to an optically active pyrimidine compound which is a liquid crystal compound useful as an electrooptic element wherein the response of the ferroelectric smectic liquid crystal to an electric field is utilized.

2. Description of the Prior Art

Liquid crystals have been employed as various electrooptic elements such as a display device of a watch or an electronic calculator. Most of liquid crystal display devices which have been put into practical use hitherto are those wherein the dielectric orientation effect of a nematic or cholesteric liquid crystal is utilized. However the application of these liquid crystals to a display device involving a large number of pixels is accompanied by some troubles such as a low response, poor contrast caused by the lack of drive margin and unsatisfactory visual angles. Therefore there has been frequently attempted to develop a MOS or TFT panel involving formation of a switching device for each pixel.

U.S. Pat. No. 4,367,924 has disclosed a liquid crystal device wherein a smectic phase based on a novel displaying principle is used to thereby overcome the disadvantages as described above.

Further it has been known that a liquid crystal compound exhibiting a C* or H phase consisting of optically active molecules generally has an electrical dipole density P and is ferroelectric. Such a chiral smectic liquid crystal having electrical dipoles is more strongly affected by an electric field than dielectric anisotropic ones. As a result, the polarity of P is made parallel to the direction of the electric field. Thus the direction of the molecules can be controlled by reversing the direction of the applied electric field. Then the average change in the direction of the major axes of these molecules is detected with the use of two polarizing plates. Thus the liquid crystal can be used as an electrooptic element.

The effect of the spontaneous polarization of this electrooptic element, wherein the response of the smectic C* or H phase to an electric field is utilized, and the electric field exert an action $10^3$ to $10^4$ times as high as those of dielectric anisotropic ones. Thus the former shows a high-speed response compared with a TN liquid crystal device. Further it is possible to impart thereto a memory function by appropriately controlling the orientation. Therefore it is expected to apply the same to a high-speed optical shutter or to a display of a large capacity.

There have been synthesized various chiral smectic liquid crystal compounds having a ferroelectricity and the properties thereof have been studied.

For example, an optically active 2-(4-alkoxyphenyl)-5-alkylpyrimidine compound and an optically active 2-(4-substituted alkoxyphenyl)-5-alkylpyrimidine compound have been proposed each as a compound which is stable to water and shows a chiral smectic phase within a wide range of temperature in Japanese Patent Laid-Open Nos. 93170/1986 and 129169/1986, respectively.

However each compound as described above is available only within a restricted range of temperature. Namely, its insufficient properties, in particular, at a low temperature make it unsatisfactory from the practical viewpoint.

SUMMARY OF THE INVENTION

It is the main object of the present invention to provide a compound useful as a liquid crystal which is suitable for preparing a composition available over an unlimited temperature range and, in particular, having a liquid crystal temperature lower than room temperature.

We have studied on a pyrimidine liquid crystal compound which shows a chiral smectic phase over a widened temperature range. As a result, we have found that an optically active pyrimidine compound of the following general formula, which has a specific alkoxy group, i.e., the alkyl group bonded to the asymmetric carbon atom substituted by a chlorine atom at the β-position, shows a chiral smectic phase over a wide range of temperature involving a low temperature region, thus completing the present invention.

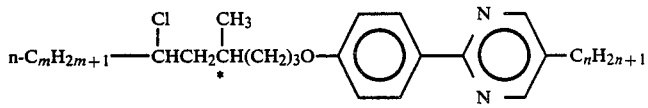

wherein
m is 1 to 12;
n is 4 to 18; and
*C represents an asymmetric carbon atom.

DETAILED DESCRIPTION OF THE INVENTION

The compound of the present invention is represented by the above general formula can be prepared by a common method used in synthesizing phenylpyrimidine compounds.

For example, it may be prepared by etherifying 5-alkyl-2-(4-hydroxyphenyl)pyrimidine with the corresponding optically active alcohol; or by etherifying 4-cyanophenol with the corresponding optically active alcohol and converting the resulting product into pyrimidine in a conventional manner.

A 5-alkyl-2-(4-hydroxyphenyl)pyrimidine compound may be prepared by a conventional method comprising, for example, converting 4-cyanophenol into a benzyl ether in a conventional manner, converting the resulting ether into 4-benzyloxy-benzamidine hydrochloride, reacting the obtained product with an n-alkylmalonic acid diester to give a 2-(4-benzyloxyphenyl)-4,6-dihydroxy-5-n-alkyl-pyrimidine and then chlorinating and reducing the product.

The optically active 6-chloro-4-methylalkanol compound to be used as the starting material in the preparation of the compound of the present invention may be obtained by alkylating (R)-(+)-citronellic acid to give an (R)-2,6-dimethyl-8-oxoalkene-2 (cf. Japanese Patent Application No. 251129/1985 applied by us) followed by reduction of the same; or by alkylating optically active 3,7-dimethyl-6-octenal with the corresponding alkylmagnesium halide and chlorinating the optically active 2,6-dimethyl-8-hydroxyalkene thus obtained to give 2,6-dimethyl-8-chloroalkene-2 followed by oxidation and reduction tha same.

The obtained compound of the present invention as represented by the above general formula can be used alone as a liquid crystal material. Alternately it can be mixed with other liquid crystal compound(s).

To further illustrate the present invention, the following Examples will be given.

EXAMPLE 1

Synthesis of 2-(4-(6-chloro-4-methyloctoxy)-phenyl)-5-n-decyl-pyrimidine (1) Preparation of 6-chloro-4-methyloctanol 18.2 g of optically active 2,6-dimethyl-8-oxodecene was dissolved in 50 ml of ethanol. 1.9 g of sodium borohydride was added thereto within five minutes at room temperature and the resulting mixture was stirred at room temperature for two hours.

The reaction mixture was sufficiently concentrated and 50 ml of water was added thereto. Then the mixture was extracted with ether, washed with a saturated saline solution and dried. After distilling off the solvent, the residue was distilled to thereby give 15.5 g of 2,6-dimethyl-8-hydroxydecene-2 as a fraction having a boiling point of 79° to 80° C. under a pressure of 1 mmHg.

13.8 g of the 2,6-dimethyl-8-hydroxydecene-2 was dissolved in 75 ml of carbon tetrachloride and 21.0 g of triphenylphosphine was added thereto. The mixture thus obtained was stirred under reflux for three hours. After distilling off the solvent, the mixture was extracted with hexane. The hexane was distilled off and then the residue was distilled to thereby give 6.9 g of 2,6-dimethyl-8-chlorodecene-2 as a fraction having a boiling point of 118° to 120° C. under a pressure of 16 mmHg.

5.0 g of the 2,6-dimethyl-8-chlorodecene-2, 100 ml of methanol and 100 ml of dichloromethane were cooled together to $-40°$ C. To the mixture, oxygen gas containing 0.04 g/l of ozone was bubbled at a rate of 120 l/hr for 30 minutes. Subsequently nitrogen gas was bubbled thereto to thereby remove excessive ozone.

Then 4.2 g of sodium borohydride was added thereto at the same temperature and the resulting mixture was allowed to reach the room temperature within one hour. Subsequently it was stirred at room temperature for additional one hour. After allowing to stand overnight, 100 ml of toluene was added to the reaction mixture. Then the resulting mixture was poured into 200 ml of a 5% aqueous solution of hydrochloric acid and stirred at room temperature for one hour. The toluene phase was collected, washed with a saturated saline solution and dried. After distilling off the solvent, the residue was distilled to thereby give 3.2 g of the aimed 6-chloro-4-methyloctanol as a fraction having a boiling point of 69° to 70° C. under a pressure of 0.1 mmHg.

(2) Preparation of 2-(4-(6-chloro-4-methyloctoxy)-phenyl)-5-n-decylpyrimidine 6-chloro-4-methyloctyl tosylate was obtained by tosylating 1.8 g of the 6-chloro-4-methyloctanol as prepared in (1) with the use of 2.1 g of toluenesulfonyl chloride and 1.2 g of triethylamine in a conventional manner.

1.0 g of 2-(4-hydroxyphenyl)-5-n-decylpyrimidine, 0.19 g of finely powdered sodium hydroxide and 10 ml of methyl ethyl ketone were stirred together under reflux for one hour. Then 1.6 g of the tosylate as described above was added thereto and the resulting mixture was further stirred under reflux for eight hours. After removing the solvent, diethyl ether was added to the residue and the obtained mixture was neutralized in a 5% aqueous solution of hydrochloric acid. After removing the solvent, 1.5 g of a pale yellow and oily product was obtained. The product was purified on a silica gel column with the use of hexane/ether (9/1) as a developing solvent. Thus 1.4 g of 2-(4-(6-chloro-4-methyloctoxy)phenyl-5-n-decylpyrimidine having a purity of 99.8% was obtained.

Infrared spectroscopy (cm$^{-1}$): 2940(vs), 2860(s), 1610(s), 1585(s), 1540(w), 1515(w), 1460(m), 1430(vs), 1380(w), 1330(w), 1330(w), 1255(vs), 1170(s), 1105(w), 1020(m), 930(vw), 845(w), 800(m), and 610(w).

This compound was poured into a transparent glass electrode cell of 2 μm in thickness, which had been subjected to orientation by rubbing, and heated to 90° C. to thereby give an isotropic liquid.

The liquid crystal cell thus obtained was cooled under a crossed Nicol prism while applying rectangular pulses (15 V. 1 Hz) thereto. As a result, definite switching behaviors were observed within a temperature range of 28.5° C. to $-5°$ C.

Further the following phase transition was observed under a polarization microscope:

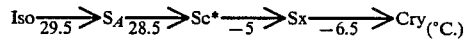

It has been confirmed that the above compound of the present invention shows an Sc* phase over a wide temperature range, i.e., over 30° C. involving a temperature as low as $-5°$ C., which obviously suggests that it is suitable for the preparation of a composition showing a low liquid crystal temperature.

In contrast thereto, each of the compounds as described in Japanese Patent Laid-Open No. 93170/1986 and No. 129169/1986 having an ethyl group as the alkyl group bonded to the asymmetric carbon atom shows an Sc* phase at a temperature exceeding approximately 15° C., when employed alone. Thus the physical properties thereof at a low temperature are unsatisfactory.

EXAMPLE 2

Synthesis of 2-(4-(6-chloro-4-methylnonyloxy)-5-n-decylpyrimidine

The procedure of Example 1 was followed except that the 6-chloro-4-methyloctanol was replaced by 6-chloro-4-methylnonanol to thereby give the title compound.

Infrared spectroscopy (cm$^{-1}$): 2940(vs), 2860(s), 1610(s), 1585(s), 1540(w), 1515(w), 1460(m), 1430(vs), 1380(w), 1330(w), 1330(w), 1255(vs), 1170(s), 1105(w), 1020(m), 930(vw), 845(w), 800(m), and 610(w).

This compound was poured into a transparent glass electrode cell of 2 μm in thickness, which had been subjected to orientation by rubbing, and heated to 90° C. to thereby give an isotropic liquid.

The liquid crystal cell thus obtained was cooled under a crossed Nicol prism while applying rectangular pulses (15 V. 1 Hz) thereto. As a result, definite switching behaviors were observed within a temperature range of 27.5° C. to $-7.5°$ C.

Further the following phase transition was observed under a polarization microscope:

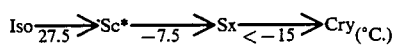

It has been confirmed that the above compound of the present invention shows an Sc* phase over a wide temperature range, i.e., 35° C. involving a temperature as low as −7.5° C. and that it shows an Sx phase under the Sc* phase and maintains the smectic domain state even at a temperature of −15° C. or below, which obviously suggests that it is suitable for the preparation of a composition showing a low liquid crystal temperature.

EXAMPLE 3

Synthesis of 2-(4-(6-chloro-4-methyloctoxy)phenyl)-5-n-octyl-pyrimidine

The procedure of Example 1 was followed except that the 2-(4-hydroxyphenyl)-5-n-decylpyrimidine was replaced by 2-(4-hydroxyphenyl)-5-n-octylpyrimidine to thereby give the title compound.

Infrared spectroscopy (cm$^{-1}$): 2940(vs), 2860(s), 1610(s), 1585(s), 1540(w), 1515(w), 1460(m), 1430(vs), 1380(w), 1330(w), 1330(w), 1255(vs), 1170(s), 1105(w), 1020(m), 930(vw), 845(w), 800(m), and 610(w).

The following phase transition was observed under a polarization microscope:

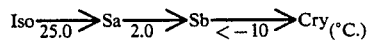

Thus the compound of the present invention is useful as a liquid crystal compound suitable for the preparation of a composition having a liquid crystal temperature lower than room temperature and as a blending agent suitable for the preparation of a composition having a liquid crystal temperature lower than room temperature.

What is claimed is:

1. An optically active pyrimidine compound represented by the following general formula:

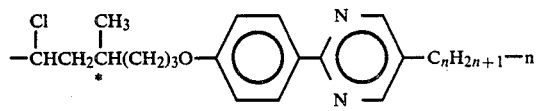

wherein
m is 1 to 12;
n is 4 to 18; and
*C represents an asymmetric carbon atom.

2. A pyrimidine compound as set forth in claim 1, which is 2-(4-(6-chloro-4-methyloctoxy)-phenyl)-5-n-decylpyrimidine.

3. A pyrimidine compound as set forth in claim 1, which is 2-(4-(6-chloro-4-methylnonyloxy)-phenyl)-5-n-decylpyrimidine.

4. A pyrimidine compound as set forth in claim 1, which is 2-(4-(6-chloro-4-methyloctoxy)-phenyl)-5-n-octylpyrimidine.

* * * * *